United States Patent [19]

Frei et al.

[11] 4,291,708

[45] Sep. 29, 1981

[54] APPARATUS AND METHOD FOR DETECTION OF TUMORS IN TISSUE

[75] Inventors: Ephraim H. Frei; Bruce D. Sollish, both of Rehovot, Israel

[73] Assignee: Yeda Research & Development Co. Ltd., Rehovot, Israel

[21] Appl. No.: 956,926

[22] Filed: Nov. 2, 1978

[30] Foreign Application Priority Data

Nov. 2, 1977 [IL] Israel ........................................ 53286

[51] Int. Cl.³ ............................................... A61B 5/05
[52] U.S. Cl. .................................. 128/734; 324/57 R
[58] Field of Search .................. 128/630, 653, 734; 324/57 R, 575 S, 60 R, 62 R, 65 R; 364/481–482

[56] References Cited

U.S. PATENT DOCUMENTS

| | | | |
|---|---|---|---|
| 3,147,750 | 9/1964 | Fry ........................................ | 128/642 |
| 3,452,743 | 7/1969 | Ricke ..................................... | 128/713 |
| 3,655,302 | 5/1972 | Lees et al. ........................... | 324/71 R |
| 3,834,374 | 9/1974 | Ensovian .............................. | 128/734 |
| 3,871,359 | 3/1975 | Pocela .................................. | 128/734 |
| 3,920,003 | 11/1975 | Ash et al. ............................. | 128/738 |
| 3,980,073 | 9/1976 | Show .................................... | 128/734 |
| 3,980,077 | 9/1976 | Shaw .................................... | 128/734 |
| 3,984,766 | 10/1976 | Thornton ........................... | 324/57 R |
| 3,990,436 | 11/1976 | Ott ........................................ | 128/734 |
| 4,038,975 | 8/1977 | Vrana et al. ........................... | 324/62 |

FOREIGN PATENT DOCUMENTS

| | | | |
|---|---|---|---|
| 618405 | 2/1949 | United Kingdom ................. | 128/734 |
| 842863 | 7/1960 | United Kingdom ................. | 128/734 |
| 903108 | 8/1962 | United Kingdom ................. | 128/734 |
| 990296 | 4/1965 | United Kingdom ................. | 128/734 |
| 1018188 | 1/1966 | United Kingdom ................. | 128/734 |

OTHER PUBLICATIONS

Bell, D. J. et al., "A Computer Based, 4-Terminal Impedance Measuring System for Low Frequencies", Journ. of Phys. E-Sci. Instr. 1975 vol. 8 pp. 66-70.
Graham, M., "Semis Invade Medical Transducers: M P Monitors EKG and BP", *Electronics Design* vol. 24 No. 19 p. 2813/Sep. 1976.
Robillard, P. et al., "Specific Impedance Measurements of Brain Tissues", MBE & Computing 1977 vol. 15 pp. 438-445.
Polczynski, M. H. et al., "Low Freq. 4-Probe Impedance Measuring System", MBE & Computing vol. 15, Sep. 1977 pp. 573-574.
Swanson, D. K. "Measurement Errors and Origin of Electrical Impedance Changes in the Limb", Thesis Submitted to Grad. Sch. Univ. of Wisc. at Madison, May 1976 Chapter 9 pp. 180-195.
Henderson, R. P. "An Impedance Camera for Spotially Specific Measurements of the Thorax", IEEE Trans. on Biomed. Engr. vol. BME-25, No. 3, May 1978 pp. 250-254.
Stibitz G. R. et al., "A Computer-Aided Bridge for Impedance Measurements in Biological Tissues", MBE vol. 12 No. 1. Jan. 1974 pp. 100-104.
Yamamoto, Y. et al., "Dynamic System for the Measurement of Electrical Skin Impedance", MBE Eng. & Comput. 1979, 17, 135-137.
Singh, B. et al., "In Vivo Dielectric Spectrometer", Med. & Biol. Engrg. & Computing Jan. 1979 pp. 45-60.
Kief, H. "Method and Apparatus for Determining Bioenergetic Ratios", U.K. published Patent Appl. GB2009413A publ. 13 Jun. 1979.
Tasto, M. et al., "Method and Device for Determining the Internal Structure of a Body, for Example a Human Body", U.K. published Patent Appl. GB2019579A.

*Primary Examiner*—Robert W. Michell
*Assistant Examiner*—Francis J. Jaworski
*Attorney, Agent, or Firm*—Browdy and Neimark

[57] ABSTRACT

An apparatus for detecting tumors in living human breast tissue includes instrumentalities for determining the dielectric constants of a plurality of localized regions of living human breast tissue. These instrumentalities include a bridge which is provided with a circuit for automatically nulling the bridge while in operation. Instrumentalities are provided for measuring variations in the dielectric constants over a plurality of the regions and for indicating the possible presence of a tumor as result of the measurement. The apparatus may be utilized in carrying out a method of detecting tumors which includes the steps of applying a plurality of probe elements to human breast tissue for sensing characteristics of localized regions thereof, applying an electrical signal to the probe elements for determining dielectric constants of localized regions of the tissue, sensing variations in the dielectric constants and determining the rate-of-change of dielectric constant at each of the localized regions.

16 Claims, 10 Drawing Figures

APPARATUS AND METHOD FOR DETECTION OF TUMORS IN TISSUE

FIELD OF THE INVENTION

The present invention relates to apparatus and methods for the detection of breast cancer and to the detection of tumors in living tissue generally.

BACKGROUND OF THE INVENTION

Breast cancer is one of the most pernicious diseases in women. This disease, which is the most common cancer of women and which now attacks one woman in 13, has had a stationary death rate for forty years in spite of advances in surgical techniques, radiotherapy and chemotherapy. In fact, if one considers that one-third of women afflicted present themselves with inoperable breast cancer, only 25% or less of women with breast cancer are alive and well ten years after diagnosis.

The probability of primary prevention of the disease by a vaccine or by environmental control, such as change in nutrition is poor for the immediate future. The outlook for a wonder drug or other remedy to cure the disease at any stage is not promising. It is known however, that our present methods of surgery, radiotherapy and chemotherapy are effective for long-term survival if applied when the disease is localized to the breast. Since many of the breast cancer cases are not localized when first seen by the clinician, a means must be found to have women present themselves for examination with their disease at an earlier stage than is commonly the case. This means in a practical way, detection of preclinical cancer in apparently "well" women, when the disease is unsuspected by patient or physician—as is the case in mass screening.

This concept is pointed up by the one-third reduction in mortality achieved in the large-scale screening program for breast cancer detection conducted by the Health Insurance Plan of Greater New York, under contract with the National Cancer Institute. (The Guttman Breast Diagnostic Institute in New York has conducted this project and most of the basic statistical information given here is taken from Prof. Strax, the head of this Institute).

On initial examination of large group of women, the number of prevalent cancers present is high, depending on such factors as self-selection and age of women. Because cancers have been present for varying lengths of time, only half of the cancers are free of nodal involvement. On subsequent examination however, the number of interval cancers i.e., cancers, which have become detectable since the previous examination, is much less and the majority have no nodal spread.

There are usually two steps in the diagnosis of breast cancer. First the detection of a lesion by a screening method, (or symptom like pain) and then narrowing down the diagnosis, first by non invasive methods and finally by biopsy, which when positive, is mostly followed by immediate surgical removal of the breast. Such factors as time of examination, radiation dose or cost of the study assume minor roles when evaluating a lesion which has already been detected.

In screening for breast cancer, however, large numbers of women are involved in a program who presumably have no disease or have only minimal symptoms. These women would not be having the examinations were it not for the opportunity offered by the screening program. The major thrust in screening is not, therefore, differential diagnosis of a lesion, but the step preceding that—detection of an abnormality. All one does in mass screening must be directed to the following objective: the initial detection of an abnormality in the simplest, safest, most accurate and most economical manner possible. The information gathered must then be passed along to the woman's medical adviser for him to proceed to a differential diagnosis on the way to proper treatment.

At present the following methods are used for the detection of breast cancer in most clinics: (1) Clinical examination including: a. Manual palpation, b. Appearance of the skin, c. Deformation of the breast; (2) X-rays (there are several variants available); (3) Thermography.

None of these methods is satisfactory by itself, neither are combinations of these methods fully satisfactory. Cancerous tumors are detected in most cases when several years old. It should also be added that final and reliable diagnosis is only done by biopsy. In many institutions positive diagnosis is obtained in only 25% of biopsies done. It seems therefore obvious that better physical methods for screening of a large number of patients as well as more reliable diagnosis before biopsy would be very important. The present technology and the large number of patients involved make computer aided devices methods of choice.

Of the presently used methods only thermography lends itself to computerized automation. A project in that field has been conducted by Prof. Anliker at the E. T. H. Zurich. Success is limited by the rather small number of tumors that cause rise in temperature of the skin. For several years a group at the Massachusetts Institute of Technology has been trying to use microwave emission in an analogous way. This would allow finding deeper-lying temperature changes. But difficult signal-to-noise problems allow only measurements of a few points in a reasonable time.

In a thesis entitled Measurement Errors and Origin of Electrical Impedance Chages in the Limb by David Keith Swanson at the University of Wiscon-Madison, at Chapter IX there is a discussion of an impedance camera employing a multi-element probe for performing measurements of the thorax. Operation at swept frequencies is suggested. There is no disclosure of a swept frequency apparatus of this type nor of the importance of the rate of change of conductance or capacitance as a function of frequency as providing information independent of extraneous factors.

SUMMARY OF THE INVENTION

There is provided in accordance with an embodiment of the present invention apparatus for detecting tumors in living human breast tissue comprising apparatus for determining the dielectric constant of localized regions of living human breast tissue and apparatus for indicating variations in the dielectric constant over a plurality of such regions, said variations indicating the possible presence of a tumor.

Further in accordance with an embodiment of the invention there is providing apparatus for determining the variation of the dielectric constant of localized regions of living human breast tissue as a function of frequency of a signal applied thereto.

BRIEF DESCRIPTION OF THE DRAWINGS

The invention will be more fully understood and appreciated from the following detailed description, taken in conjunction with the drawings in which.

DETAILED DESCRIPTION OF THE INVENTION

Figure 1:
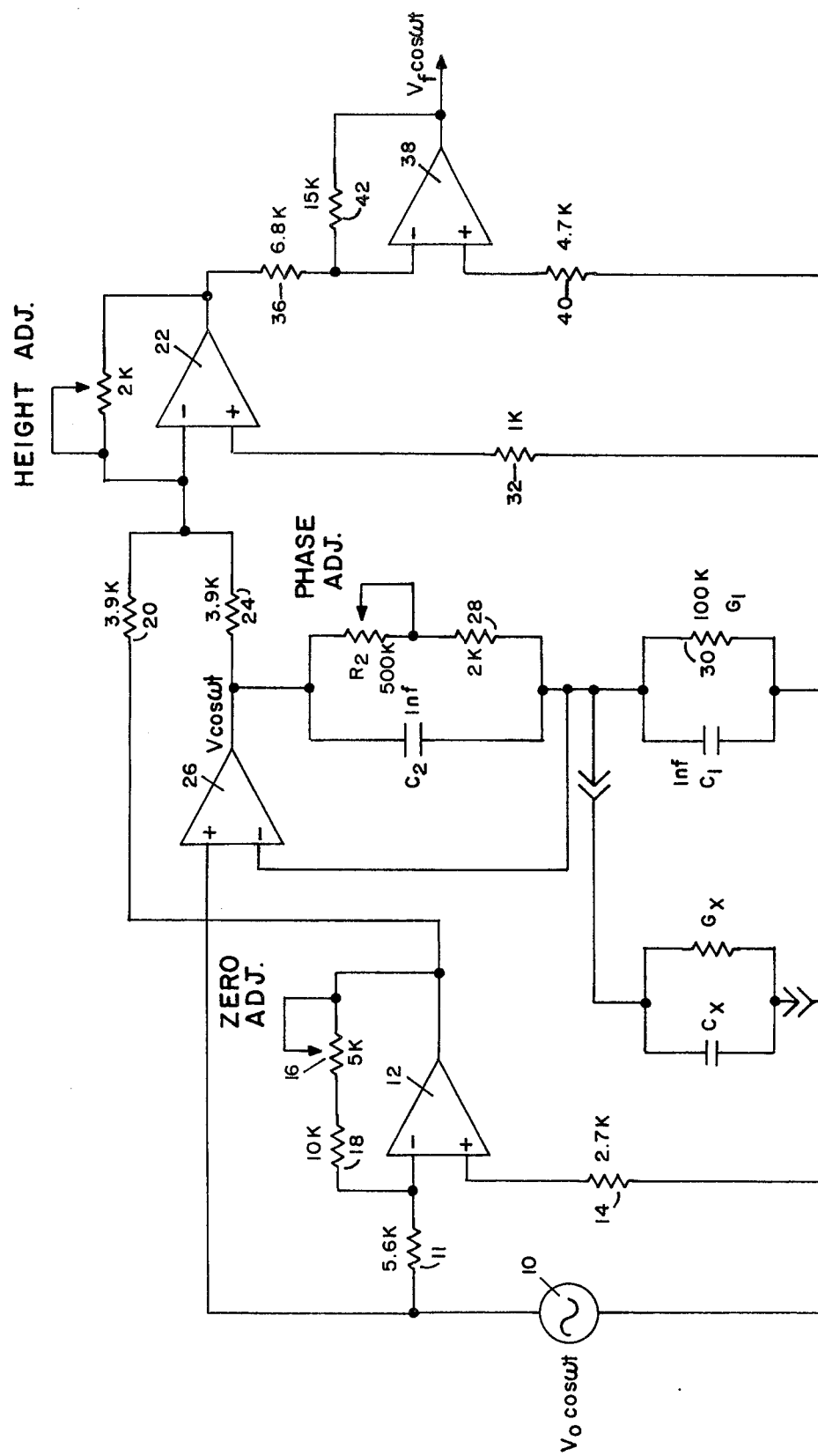
FIG. 1 is a schematic illustration of a detector circuit constructed and operative in accordance with an embodiment of the invention.

The electrical properties of tissue have been studied extensively by Schwan, H. P., Electrical Properties of Tissue and Cell Suspensions, in *Advances in Biological and Medical Physics Vol. V.*, ed. by J. H. Lawrence and C. A. Tobias, (Academic Press, New York, 1957), pp. 147-209; Schwan, H. P. and Kay, C. F., Capacitive Properties of Body Tissues, *Circulation Research Vol. V*, (July 1957), pp. 439-443; and Schwan, H. P. and Sittel,. K., Wheatstone Bridge for Admittance Determinations of Highly Conducting Materials at Low Frequencies, *Trans. AIEE* 72, 114 (1953). It has been found that fatty tissue exhibits significantly different dielectric constant and conductivity than muscle tissue. Since most cancer develops in post-menopausal women (assumed in the age 50 and up group), and since the post-menopausal breast is characterized by a proliferation of adipose (fatty) tissue, it may be possible to detect cancer in the post-menopausal breast by in situ measurement of the appropriate electrical parameters. It is assumed, therefore, that the problem of detecting a tumor in the breast reduces to that of detecting a small region characterized by certain electrical characteristics embedded in a larger region of different electrical characteristics (essentially, those of fat).

The present devices provide means of measurement of dielectric constant and conductivity in the breast. By examining different portions of the breast, and by comparing the dielectric constants and conductivities measured, a region containing a possible tumor can be identified through changes in dielectric constant and/or conductivity.

The electric field E within the breast due to the applied external field supplied by the probe satisfies the Laplace equation: $\nabla^2 E = 0$. At every location within the breast, the dielectric displacement D is related to the electric field E by the complex dielectric constant $\epsilon$ as $D = \epsilon E$. The complex dielectric constant includes a real part (the dielectric constant) and an imaginary part, the losses, related to conductivity.

Different dielectric constants within the breast combine to influence the impedances as measured by the multielectrode probe, according to the Laplace equation and the appropriate boundary conditions. Hereinafter in the specification and the claims, the term dielectric constant shall be taken to mean the complex dieletric constant, the real or imaginary part thereof or electrical properties related thereto.

The purpose of the invention is therefore to enable detection possible turmors in the breast. The method is safe, non-invasive, and does not require injection of contrast materials. The devices provided give quantitative information which can be used in conjunction with any or all of the present-day diagnostic techniques (palpation, X-ray, thermography). Finally, it can be used as a prescreening technique before a decision is taken to send the screenee to mammography.

While it is realized that many variations of techniques can be and have been utilized for measuring electrical properties of tissues, the present devices represent specific configurations and implementations suitable for use in breast cancer screening. Since electrical properties of tissues vary markedly with frequency, several versions of the device are described for low frequency and high frequency operation.

Reference is now made to FIG. 1 which shows detection circuitry constructed and operative in accordance with an embodiment of the invention and comprises a half-bridge circuit across which is coupled, via contact with a probe, the unknown capacitance $C_x$ and unknown conductance $G_x$ of a tissue region to be measured. The unknown capacitance and conductance of the tissue region to be measured are indicated as a parallel RC combination selectably couplable at one terminal to a bus A which is connected to one terminal of AC voltage source 10 and may be coupled to ground.

An operational amplifier, 12, has a negative input coupled to a second terminal of AC voltage source 10 across a resistor, 11, typically of value 5.6 K. The positive input to amplifier 12 is coupled to bus A via a resistor 14, typically of value 2.7 K. The output of amplifier 12 is fed back to the negative input thereof via a variable resistor 16, operative as a zero adjustment, and a fixed resistance 18, typically of value 10 K. The output of amplifier 12 is also supplied via a resistor 20, typically of value 3.9 K to a negative input of an operational amplifier 22. The negative input to amplifier 22 also receives an input via a resistor 24, typically of value 3.9 K from the output of an operational amplifier, 26, whose positive input is coupled to the junction of voltage source 10 and resistor 11. The negative input of amplifier 26 is coupled to the output thereof across a parallel combination of a capacitor $C_2$, typically of capacitance 1 nf and a pair of series connected resistances 28, typically of value 2 K and $R_2$, a variable resistor which functions to provide phase adjustment of the output signal. The negative input to amplifier 26 is also coupled to the aforesaid unknown capacitance and conductance via the probe and also to a parallel RC combination comprising a capacitor $C_2$ of typical value 1 nf and a resistor 30 of typical value 100 K.

The positive input to amplifier 22 is coupled across a resistor 32, typically of value 1 K to bus A. The output of amplifier 22 is fed back to the negative input thereof via a variable resistor 34 which is employed to provide height compensation. The output of amplifier 22 is also applied across a resistor 36 to the negative input of an operational amplifier 38, whose positive input is coupled across a resistor 40, of typical value 4.7 K to bus A. The output of operational amplifier 38 is fed back to the negative input thereof via a resistor 42, typically of value 15 K. When the circuit is adjusted for zero phase shift the output of amplifier 38 is given as $V_f \cos \omega t$.

At low frequencies, electrical properties of tissue are primarily resistive (Schwan, H. P. Electrical Properties of Tissue and Cell Suspensions, in *Advances in Biological and Medical Physics Vol. V.*, ed. by J. H. Lawrence and C. A. Tobias, (Academic Press, New York, 1957), pp. 147–209.). The device in FIG. 1, is suitable for tissue measurements from 100 Hz–10 kHz. A half-bridge arrangement is employed using parallel RC elements. Before beginning a measurement, the circuit is zeroed by adjustment of potentiometer $R_2$.

The gain of the half-bridge is given by $$V/V_o = 1 + Y_1/Y_2 \quad (1)$$

$$= 1 + \frac{G_1'G_2 + \omega^2 C_1'C_2 + j\omega(C_1'G_2 - G_1'C_2)}{G_2^2 + (\omega C_2)^2}$$

where $G_1' = G_1 + G_x$ and $C_1' = C_1 + C_x$

In the absence of an external $C_x$-$G_x$ circuit (the examined tissue), if $G_1 = G_2$ and $C_1 = C_2$, $V/V_o = 2$. The final output is therefore zero. Upon making an examination, the balance of the circuit is upset. Since the body conductance is significant in the low frequency range, it is necessary to compensate for the phase-shift it induces. This is done by setting $G_2 = (C_2/C_1') \cdot G_1'$. The gain function $V/V_o$ then reduces to $V/V_o = 1 + C_1'C_2$. If the unknown body capacitance is $C_x$ and the unknown conductance is $G_x$, the output voltage is $V/V_o = 2 + C_x/C_2$. The unknown capacitance can be found from the output voltage, and from this and from the measured value of $G_2$, the unknown conductance can be found as well. That is $$C_x = (V/V_o - 2) \cdot C_2 \quad (2)$$
and
$$G_x = (V/V_o - 2) \cdot G_2$$

Figure 5:
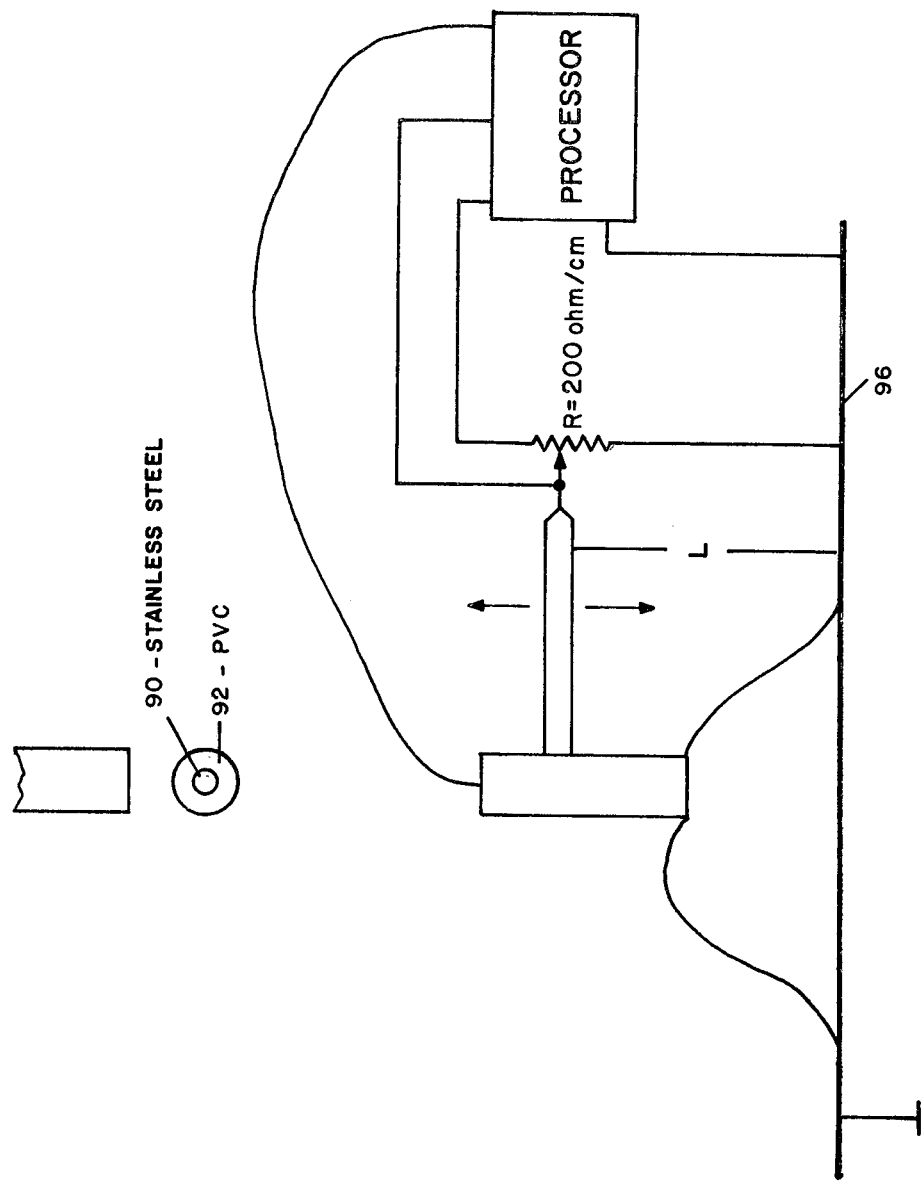
FIG. 5 is a schematic illustration of a detector associated with a subject being examined.

With circuit values as given, and with the probe shown in FIG. 5, the tissue dielectric constant K is given by $V_f/V_o \times 10^5$.

The above procedure is satisfactory for examination of a few locations on the breast and/or for a limited number of different frequencies. However, for scanning many sites along the breast at many different frequencies, the method is too time-consuming to be practical. For each change in location or frequency, resistor $R_2$ must be readjusted for zero-phase shift.

Figure 2:
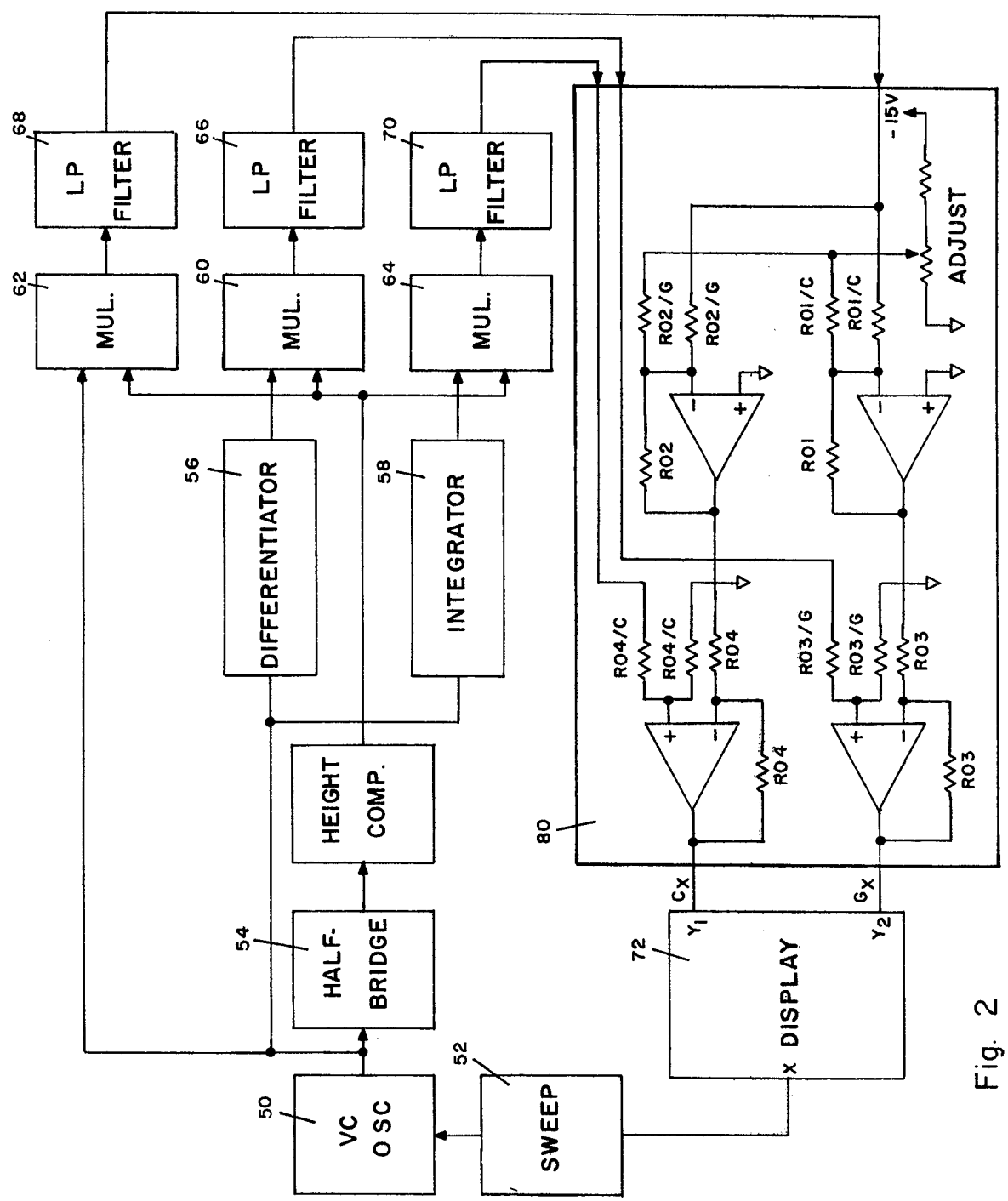
FIG. 2 is a schematic illustration of signal processing circuitry constructed and operative in accordance with an embodiment of the invention.

Apparatus for automatic calculation of $C_x$ and $G_x$ is illustrated in FIG. 2. A voltage-controlled oscillator 50 receives a control input from a ramp voltage generator 52 and provides an input voltage to a half bridge circuit 54 which is substantially similar to the circuitry illustrated in FIG. 1, except that the variable resistor R2 in FIG. 1 is replaced by a fixed resistance. The output of voltage—controlled oscillator 50 is also supplied to a differentiator 56 and to an integrator 58.

Voltage controlled oscillator 50 produces output voltage $v_o \cos \omega t$, where the frequency varies between typical limits of 0.1 KHz and 10 KHz. The differentiator 56 thus produces a signal proportional to $2\omega \sin \omega t$, and the integrator 58 produces a signal proportional to $2/\omega \sin \omega t$.

The output of half-bridge circuit 54 is supplied in parallel to first, second and third multipliers 60, 62 and 64 which respectively multiply the half bridge output V $\cos (\omega t + \phi)$ by $2\omega \sin \omega t$. $2 \cos \omega t$ and $2/\omega \sin \omega t$. The outputs of the respective multipliers 60, 62 and 64 are supplied to respective low pass filters 66, 68 and 70 in order to extract the D.C. components thereof. The D.C. voltages obtained from the respective low pass filters 66, 68 and 70 are respectively $-\omega b$, a and $b/\omega$ $$a = \frac{GG_x + \omega^2 CC_x}{G^2 + \omega^2 C^2} \quad (3)$$
where and
$$b = \frac{\omega(GC_x - CG_x)}{G^2 + \omega^2 C^2}$$

These equations can be inverted to obtain $$C_x = aC + \frac{b}{\omega} G \quad (4)$$

$$G_x = aG - \omega bC$$

where $C_x$ and $G_x$ are the unknown body capacitance and conductance.

The three D.C. voltages $-\omega b$, a and $b/\omega$ are supplied to inputs of an analog processor 80 which comprises a RC 4136 chip containing four operational amplifiers and produces voltage outputs indicating the unknown quantities $C_x$ and $G_x$ in accordance with the above equations. The $C_x$ and $G_x$ outputs are supplied to a storage display 72, together with the output of ramp voltage generator 52 which provides synchronization. The storage display desirably should be capable of displaying the $G_x$ and $C_x$ functions on an XY plane covering the body area being examined, thereby indicating clearly to the operator divergences in conductance and capacitance and thus in dielectric constant in the examined region. Displays which indicate a value such as $C_x$ or $G_x$ as a function of XY coordinates by means of color are presently in commercial use.

Reference is now made to FIG. 5 which shows in schematic illustration a probe arrangement which may be useful in the embodiments of FIGS. 1 and 2. A 1 cm² area circular stainless steel electrode 90 is encased in a layer 92 of PVC or any other suitable insulator. The patient is disposed against a grounded plate or table, as indicated schematically by the grounded plane 96. The probe is placed in contact with the body part and moved from position to position thereon in order to determine the values of $C_x$ and $G_x$ for various regions of the portion being examined.

Figure 3:
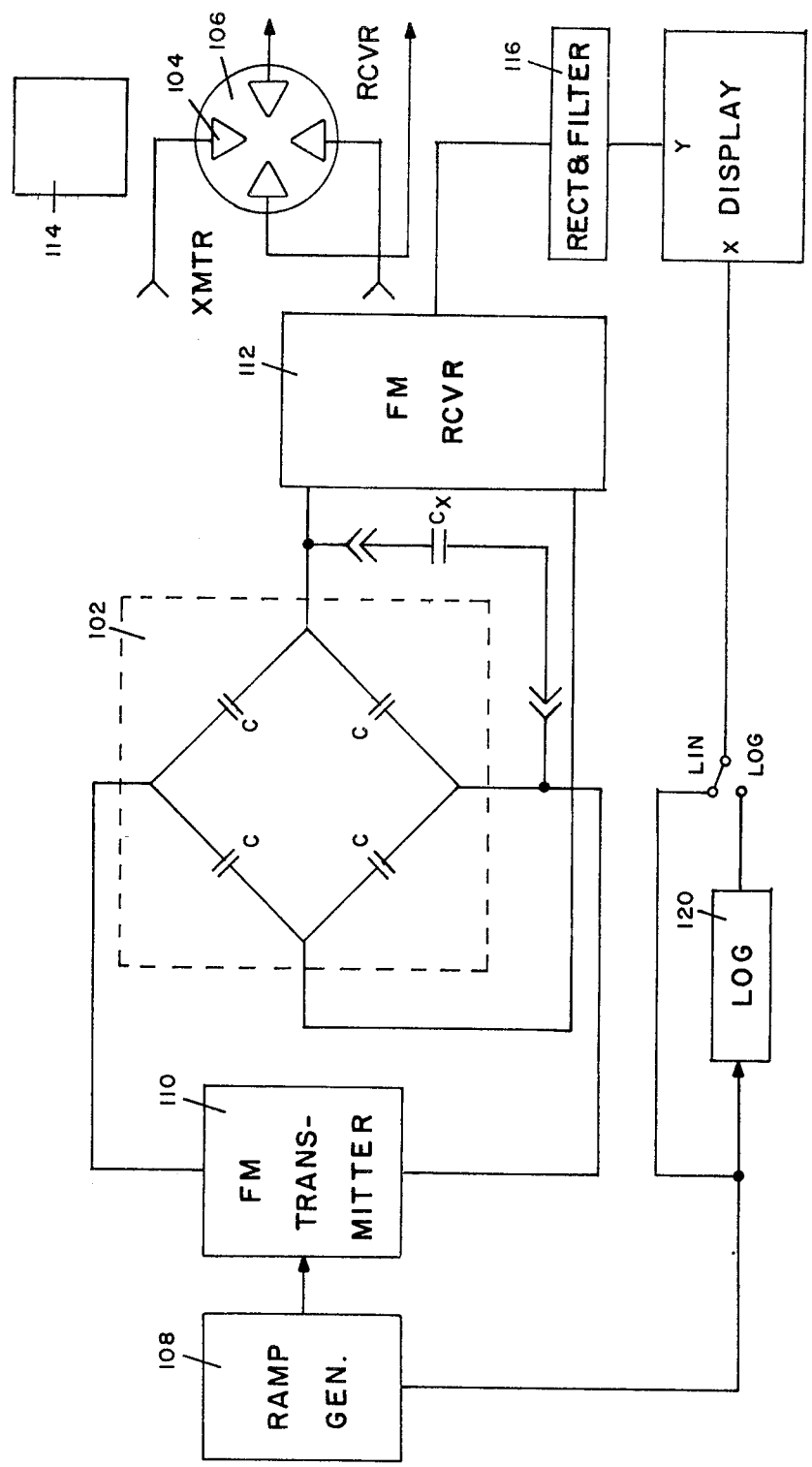
FIG. 3 is a schematic illustration of a detector circuit constructed and operative in accordance with another embodiment of the invention.

At their frequencies, from about 10 MHz, the capacitive effect is predominant in tissues. FIG. 3 shows a detector based on a capacitive bridge arrangement 102. The capacitance bridge comprises four triangular shaped electrodes 104, arranged in a symmetric circular fashion on insulating material 106 (typically PVC or Teflon) forming one end of cylindrical probe 114. A ramp generator 108 is used to modulate the carrier frequency of a 100 MHz FM transmitter with 1 kHz audio modulator whose output is fed to two opposing bridge elements. An FM receiver 112 is connected across the other two opposing bridge elements. A rectifier and filter 116 connected across the audio output of the FM receiver gives a DC voltage proportional to the audio output.

Before the probe is placed on the tissue to be examined, the bridge is balanced and the DC output of rectifier 116 is zero. When the probe is placed over tissue of an inhomogeneous nature (with respect to dielectric constant), the bridge becomes unbalanced, producing a DC output at rectifier 116. This output is fed to the Y-axis of storage display 118. Simultaneously, the ramp voltage due to 108 is fed to the X-axis of the display to give a display of $C_x$ vs $\omega$, or if a logarithmic amplifier 120 is inserted, a display of $C_x$ vs log $\omega$ results.

Figure 4:
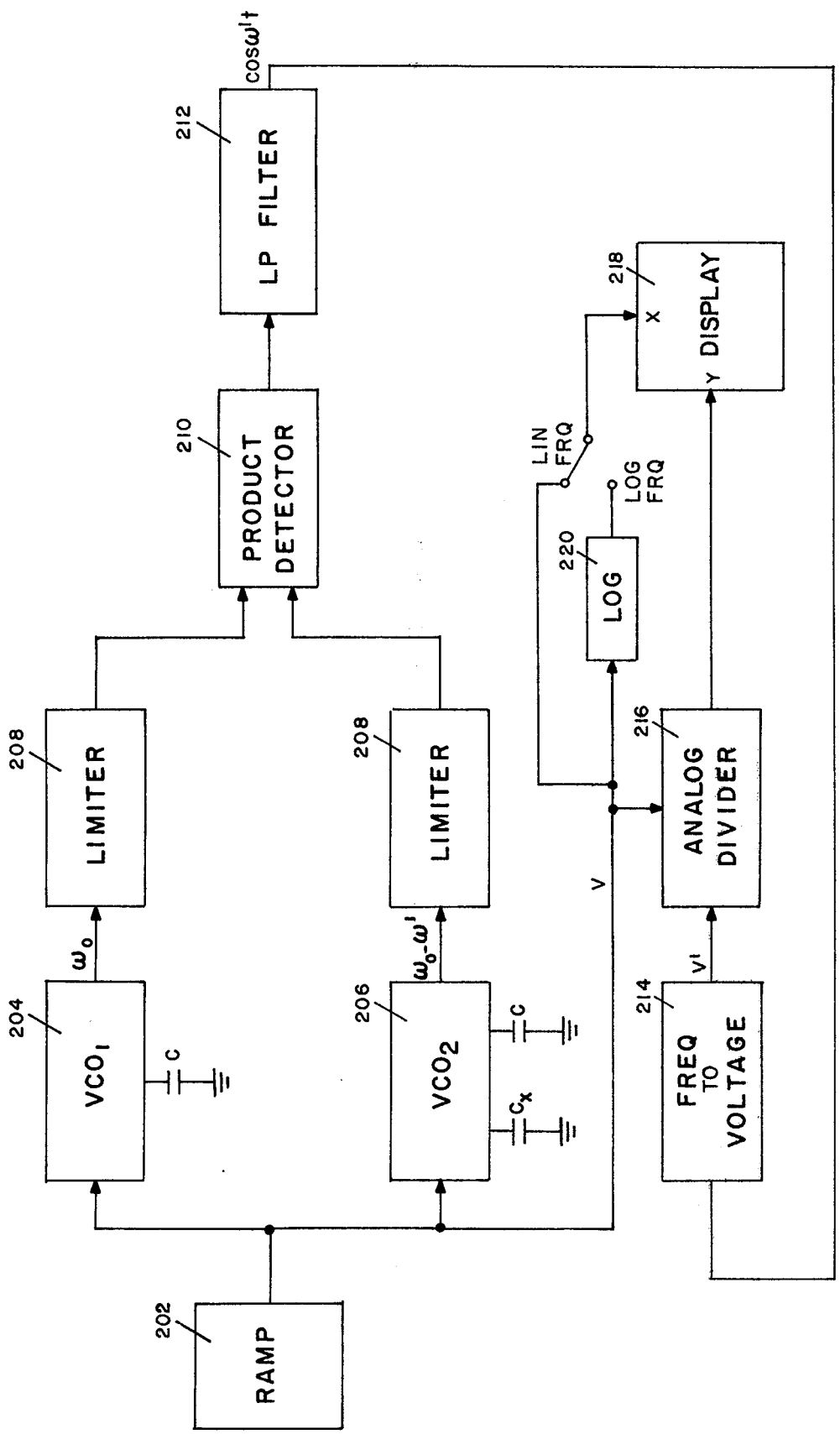
FIG. 4 is a schematic illustration of detector and signal processing circuitry constructed and operative in accordance with another embodiment of the invention.

Another high frequency detector responding to capacitive properties of tissues is shown in FIG. 4. The probe is of the type shown in FIG. 5. The heart of the detector is a pair of voltage-controlled oscillators 204 and 206. Without the tissue capacitance the two voltage-controlled oscillators oscillate at the same frequency and are balanced. When the probe is placed on tissue, the tissue capacitance adds to the capacitance C of 206 and thus lowers the oscillator frequency from $\omega_O$ to $\omega_o - \omega'$, where $$\frac{\omega'}{\omega_o} = \frac{C_x(\omega_o)}{C} \quad (5)$$

if $C_x$ is much less than C

The output of the reference oscillator 204 and signal oscillator 206 are limited by limiters 208 and then detected by product detector 210 and low-pass filter 212. The output of filter 212 is a sinusoidal waveform of frequency $\omega'$. This sinusoid is inputted to frequency-to-voltage converter 214 (essentially the reverse of a voltage-controlled oscillator) to obtain a DC voltage V' proportional to $\omega'$. The voltages V' and ramp voltage $V_o$ are divided by analog divider 216 to yield a voltage $V'/V_o$ proportional to $C_x(\omega_o)/C$ as in Equation 5. This voltage is brought to the Y-axis of storage display 218. Simultaneously, V or log V (as obtained by logarithmic amplifier 220) is brought to the X-axis of display 218, thus displaying the tissue capacitance $C_x$ as a function of frequency or of log-frequency.

Since measurement of capacitance and conductance are dependant on the thickness of the tissue measured, as well as on its electrical properties, the thickness factor must be removed from the measured results. This is done by the height-compensation potentiometer, shown explicitly in FIGS. 1, 2 and 5. The potentiometer forms part of a variable-gain circuit. The potentiometer scale factor is 200 $\Omega$/cm. At a nominal working distance of 10 cm, the variable gain circuit has a gain of 1. If the actual tissue thickness L is different from 10 cm, the gain of the variable gain circuit is L/10. This automatically compensates for signals received from the actual working distance, thus enabling comparison among measurements made at various working distances.

Figure 6:
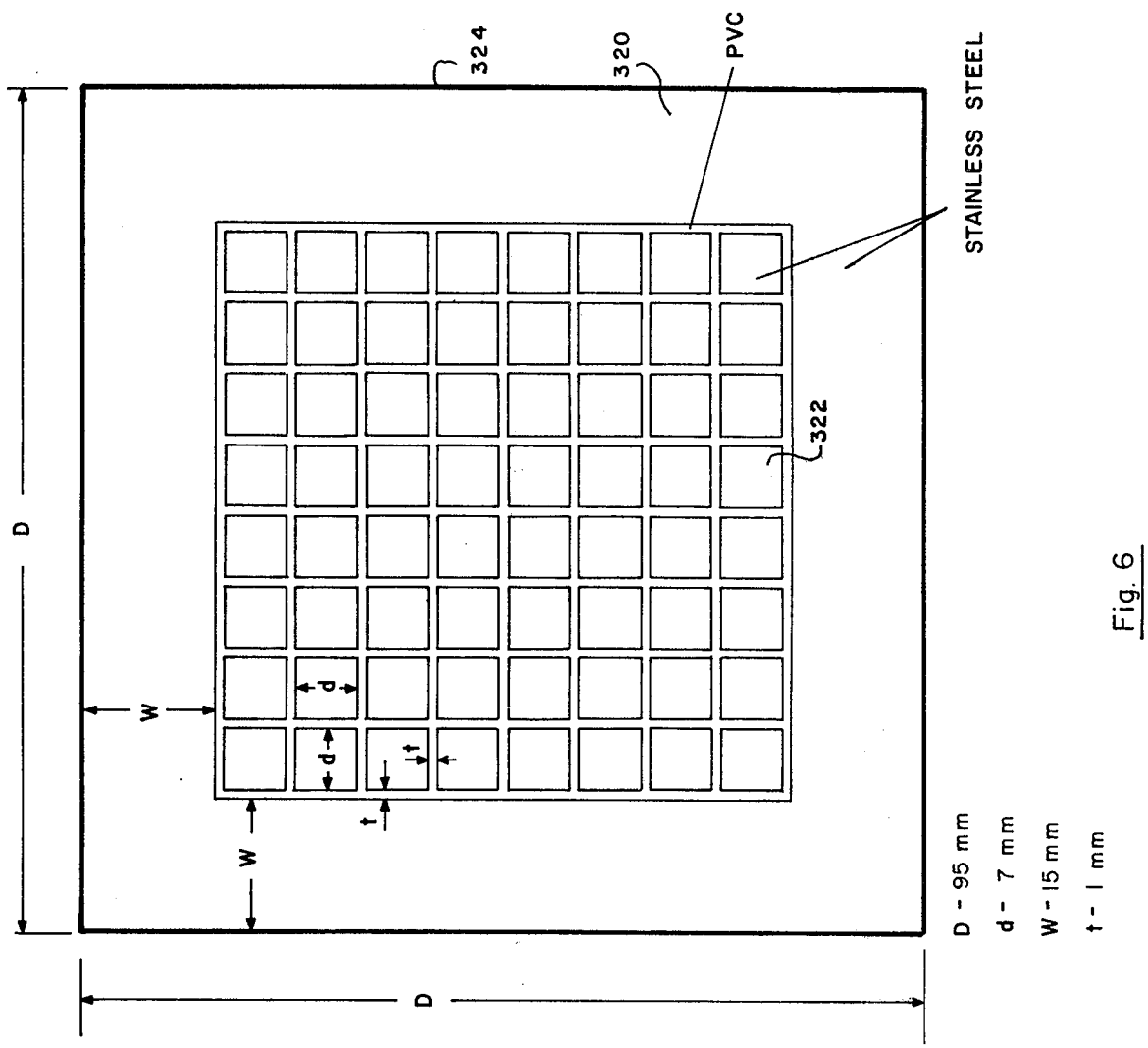
FIG. 6 is a schematic illustration of a multi-element probe used in the invention.
Figure 7:
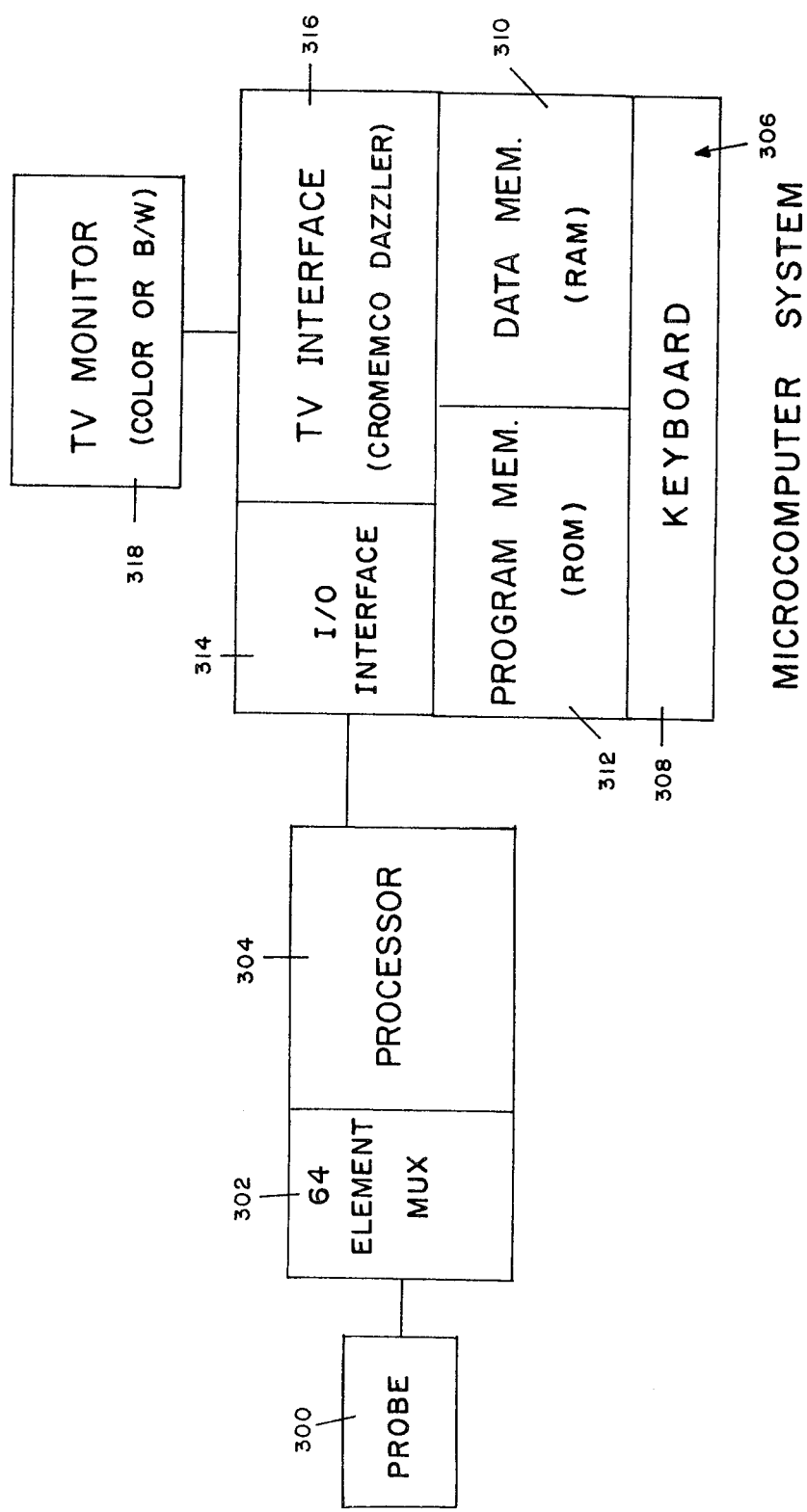
FIG. 7 is a schematic illustration of a computer-controlled breast cancer screening system.

Reference is now made to FIG. 7 which illustrates in schematic block diagram form computer-controlled breast cancer screening apparatus constructed and operative in accordance with an embodiment of the present invention. The screening apparatus comprises a multielement probe, typically comprising 64 elements arranged in an 8×8 array. This probe, indicated by reference numeral 300, will be described hereinafter in greater detail in connection with FIG. 6

Probe 300 is coupled, via a 64 element multiplexer 302 to an electronic processor 304, which will be described hereinafter in connection with FIGS. 8–10.

Electronic processor 304 interfaces with a microcomputer control and data storage and display system 306. System 306, in accordance with a preferred embodiment of the invention is embodied in a SOL 20 unit, manufactured by Processor Technology of California, U.S.A.. It is to be understood of course that any other suitable microcomputer control and data storage and display system may alternatively employed.

The SOL 20 microcomputer system is based on the Intel 8080 8-bit microcomputer and employs the well - known S -100 bus system. The SOL 20 has a built-in keyboard 308 which permits the entry of patient identification information, for example, and a 16 K byte RAM memory 310, such as a Dynabyte DY-M51645, for data storage. A program memory 312 comprises one or more 16 K programmable ROM boards such as Cromemco CR - 16K PR/A, each having 16 K bytes of eraseable ROM memory. The SOL - 20 also comprises serial and parallel input - output interfaces 314. A video interface 316, the TV Dazzler (C/CRDZ/A), also manufactured by Cromemco, is provided to generate appropriate video signals for display on a color or black and white television monitor.

The microcomputer system 306 is programmed by standard techniques to generate the required control signals for the electronic processor, to input the data obtained by the electronic processor 304 from the probe 300, and to output the data onto the TV monitor 318 in alphanumeric and graphic format.

Reference is now made to FIG. 6 which illustrates a multielement probe constructed and operative in accordance with an embodiment of the present invention. The probe comprises a base 320, formed of plastic such as PVC onto which are mounted in a generally planar arrangement 64 generally flat conductive probe elements 322, typically formed of stainless steel and each coupled via a conductor (not shown) to an input of multiplexer 302. In the preferred embodiment, the probe elements 322 are arranged in a 8×8 flat array. Alternatively, the probe elements may be of any desired number and may be arranged in any suitable array. As a further alternative, the array need not be flat and may, for example, be configured to correspond to the shape of a human breast. In the present embodiment, the array is designed to be placed over one quadrant of the breast at a time.

Surrounding the array and base 320 is a frame member 324 of stainless steel which is provided to present an equipotential surface in the region being examined. Typical dimensions of the probe are as follows:

| | |
|---|---|
| Overall width of the frame | 95 mm square |
| Overall width of the probe element | 7 mm square |
| Spacing between adjacent probe elements | 1 mm |
| Distance between edge of frame and adjacent probe elememt | 15 mm. |

It may be understood that the probe is connected to the multiplexer via 64 individual leads. It is noted that advantageous use of the probe surface area may be achieved by using hexagonal elements.

Figure 8:
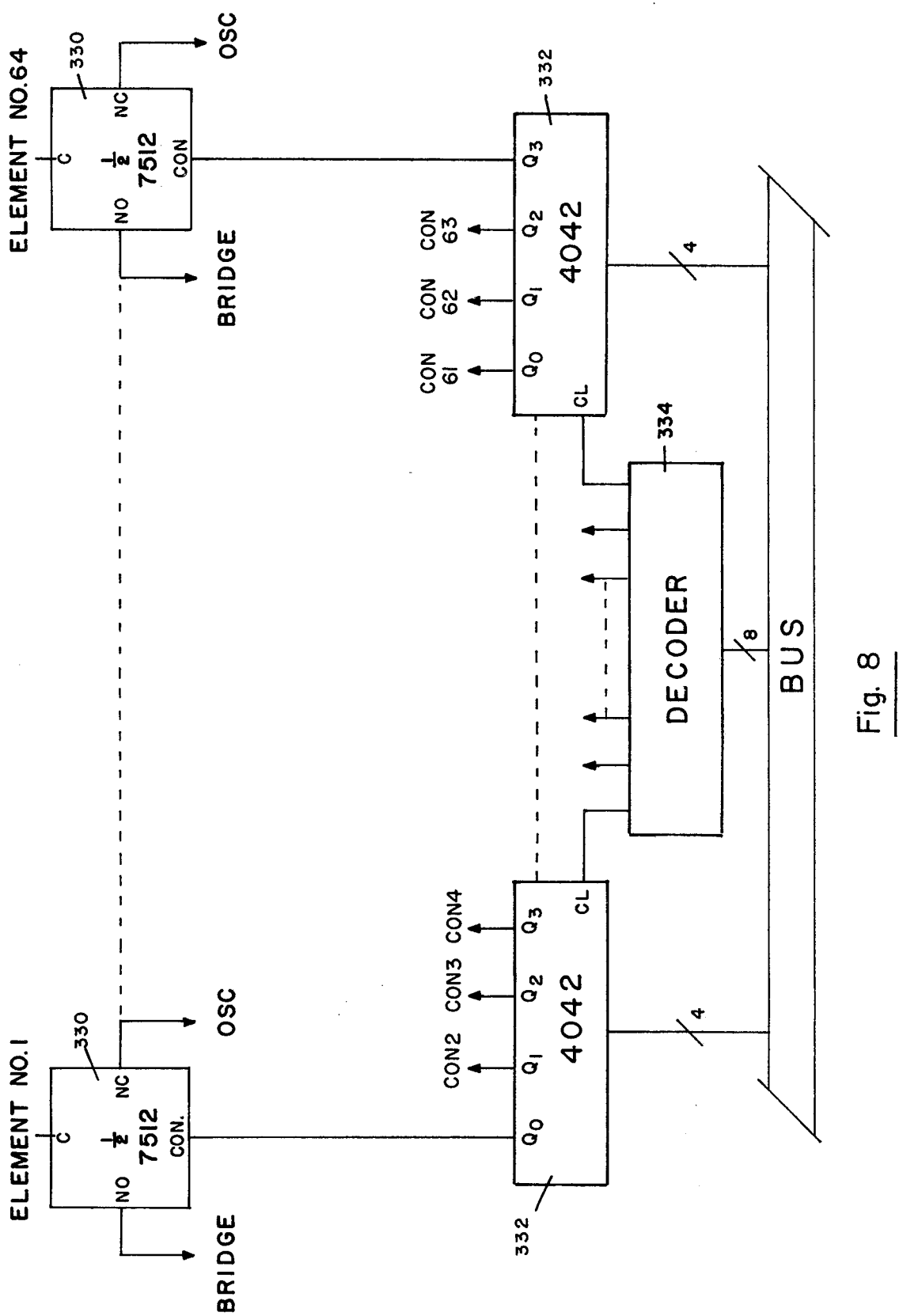
FIG. 8 is a schematic illustration of a multiplexer used in the system of FIG. 7.

Reference is now made to FIG. 8 which is a schematic illustration of the multiplexer 302. The multiplexer 302 may be understood as comprising 64 SPDT electronic switches, controlled by 64 independent control lines. Each switch is also connected to one of the 64 elements of the probe. Each switch is operative in response to a control signal received along the control line to connect a single probe element either to the bridge circuitry or to the oscillator in the electronic processor 304, as will be described hereinafter. All 64 probe elements are maintained at the same potential during an examination of a patient, however, only the individual probe element actually connected to the bridge actually contributes to the calculation of dielectric constant. It is noted that in the preferred embodiment discussed here one probe element is connected to the bridge at a time. Alternatively any suitable number of probe elements may be simultaneously connected to the bridge, provided that suitable processing circuitry is available for indicating the electrical quantities actually measured.

In accordance with the embodiment of the invention here presented, the multiplexer sequentially switches the probe elements one by one to the bridge circuitry in order to scan a plurality of regions of the patient for measuring the spatial variation in the electrical properties thereof.

FIG. 8 illustrates the first and 64'th electronic switches 330, which are typically 7512 dual SPDT analog switches made by Analog Devices. The normally-closed (NC) poles of each switch are connected to the oscillator (not shown), while the normally open (NO) poles of each switch are all connected to the bridge (not shown). The center (C) pole of each switch is connected to a corresponding probe element. Thus a total of 64 probe elements are connected to 32 identical 7512 switches.

The control (CON) terminal of each switch 330 is connected to one of the four Q outputs of a register 332 such as a 4042 4-bit latch. Thus 16 of the 4042 latches are required for controlling the 64 7512 switches. A decoder 334, of conventional construction selects the appropriate latch for setting two groups of four controls each in response to the program control provided by the microcomputer system 306. Thus eight individual 8-bit control words set the status of each of the sixty four elements.

Figure 9:
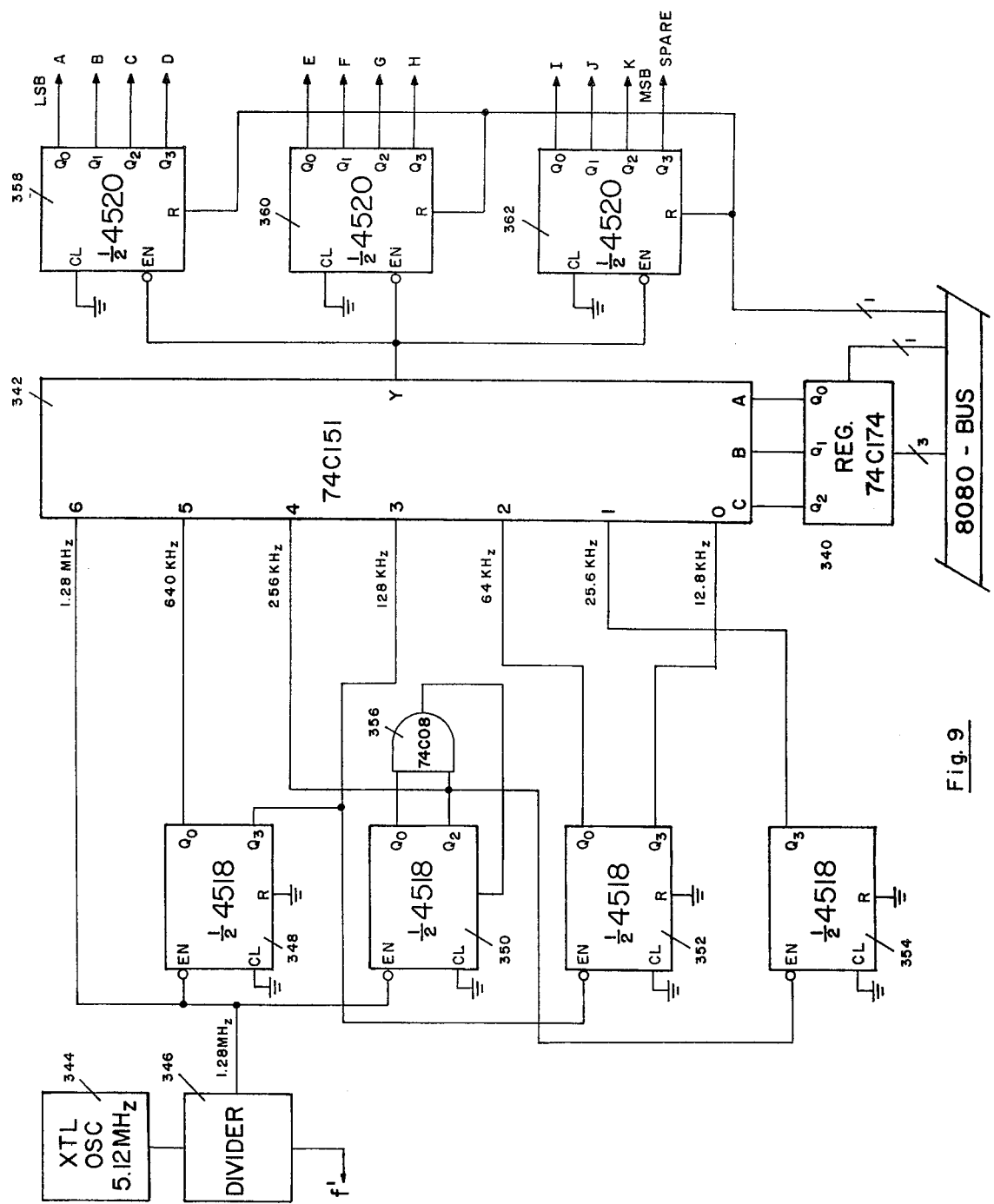
FIGS. 9 and 10 together illustrate an electronic processor used in the system of FIG. 7.
Figure 10:
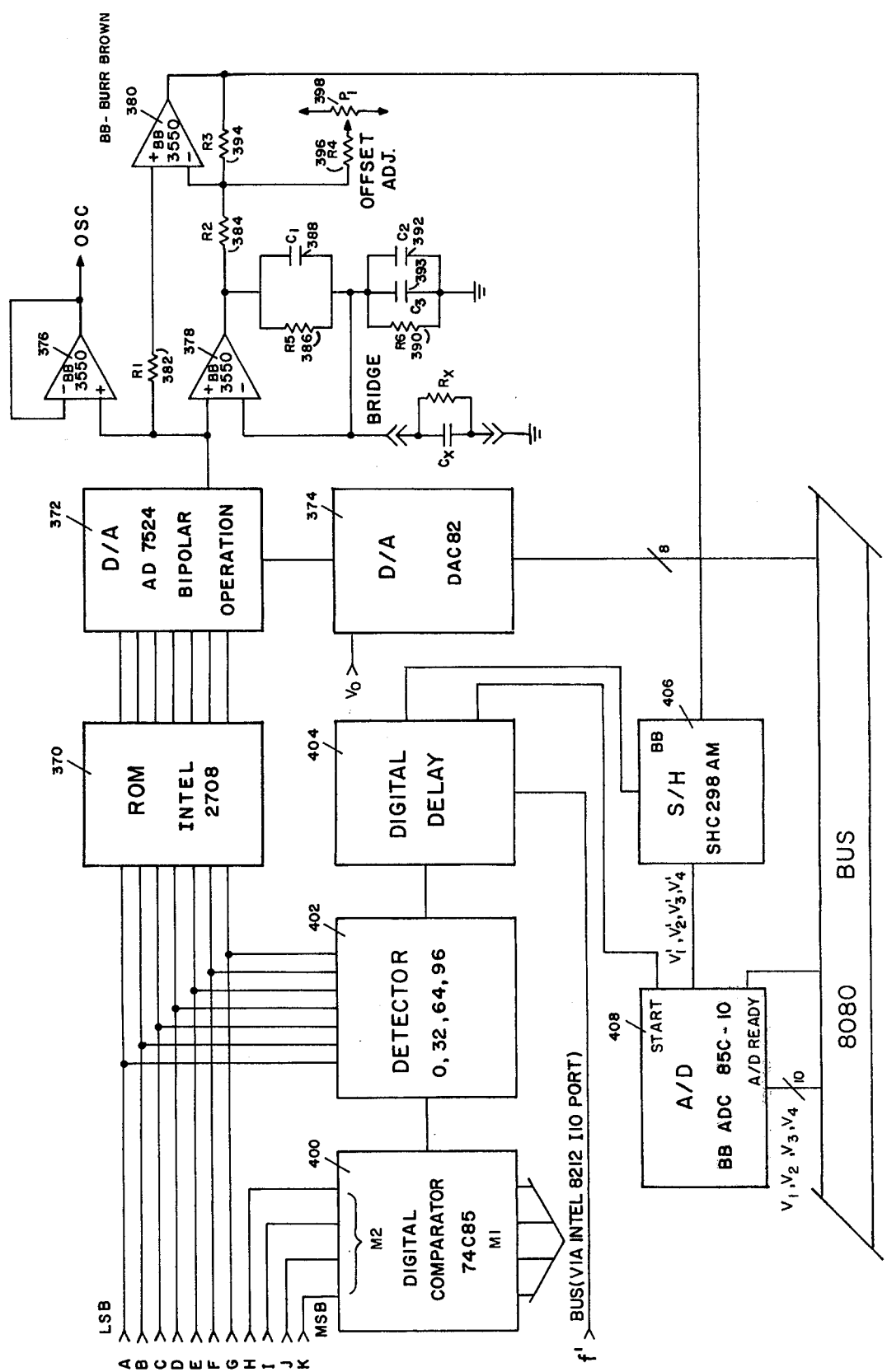

Reference is now made to FIGS. 9 and 10 which together illustrate the electronic processor. FIG. 9 illustrates a clock rate generator for using in generating seven differentfrequencies and which forms part of the electronic processor. The clock rate generator comprises a latch 340 such as a 74C174, which is operative to receive control inputs from the microcomputer system 306 under appropriate program control and in response to these control inputs, to control a 74C151 8 line to 1 line digital multiplexer 342. A standard crystal clock oscillator 344 operating at 5.12 MHz, for example, supplies an output to a divide-by-four counter 346 which reduces the clock rate to 1.28 MHz. This 1.28 MHz input is supplied to input 6 of multiplexer 342 and is also supplied to the EN inputs of two halves of a dual 4518 counter 348 and 350. The Q 0 and Q 3 outputs of counter half 348 are coupled to respective inputs 5 and 3 of the multiplexer 342 and provide respective sequences of 640 KHz and 128 KHz. The Q 3 output of counter half 348 is also supplied to EN input of a counter half 352 of a second dual BCD 4518 counter, whose second half is identified by reference numeral 354.

The Q 0 output of counter half 350 is supplied to an input of a 74C08 AND gate 356 and the Q 2 output of counter half 350 is supplied to input 4 of multiplexer 342 as a 256 KHz signal and also to the second input of AND gate 356. The output of AND gate 356 is supplied to the R input of counter half 350. The Q 2 output of counter half 350 is also supplied to the EN input of counter half 354.

The Q 0 output of counter half 352 provides a 64 KHz input to input 2 of multiplexer 342; the Q 3 output of counter half 352 provides a 12.8 KHz output to input 0 of multiplexer 342 and the Q 3 output of counter half 354 provides a 25.6 KHz output to input 1 of multiplexer 342.

Multiplexer 342 is operative to select one clock rate from among the seven inputed thereto and to apply it at an output terminal Y to an 11-bit binary counter comprising 4520 type dual 4-bit binary counters, including counter halves identified by reference numerals 358, 360 and 362. The reset inputs of counters 358, 360 and 362 are operated by the microcomputer system under appropriate program control and the Q0-Q 3outputs of the three counter halves 358, 360 and 362 are identified by the letters A–K.

Reference is now made to FIG. 9 which illustrates the remainder of the electronic processer. A programmable ROM 370 such as an Intel 2708 type, receives inputs A–G from counters 358 and 360. It is noted that input A is the least significant bit while input K is the most significant bit. Thus iputs A–G are the seven least significant bits of the output of counters 358, 360 and 362. ROM 370 is programmed to give the sine of the input in an 8-bit complementary offset binary (COB) format. Thus, if the input to the ROM is N, where $0 \leq N \leq 127$, the output of the ROM is $\sin 2\pi N/128$ in COB format. The following table indicates the translation for various values of N

| N | $\sin \frac{2\pi N}{128}$ | COB |
|---|---|---|
| 0 | 0 | 10000000 |
| 32 | +1 | 00000001 |
| 64 | 0 | 10000000 |
| 96 | −1 | 11111111 |

The 8-bit output from ROM 370 is supplied to a multiplying digital-to-analog converter 372 such as an Ad 7524 made by Analog Devices. The D/A converter is connected in the bipolar mode as described by the manufacturer, such that as the ROM is cycled over all its address inputs, the D/A converter 372 produces an analog sinewave signal, one cycle for each ROM cycle. The frequency of the sinewave output of converter 372 is 1/128 of the frequency of the clock signal present at the Y output of multiplexer 342. Thus depending on the input selected by multiplexer 342, the sinewave may be of frequency 100, 200, 500, 1000, 2000, 5000 or 10,000 Hz. The amplitude of the sinewave is determined by the voltage at a $V_{ref}$ input of converter 372.

The voltage applied to the $V_{ref}$ input is determined by an 8-bit D/A converter 374 such as a DAC 82 manufactured by Burr-Brown. D/A converter 374 has an internal fixed reference $V_o$ which is typically selected to be 5 volts. D/A converter 374 receives from the microcomputer system under suitable program control an 8 bit gain word K, where K is in the range of between 1 and 255. The output of D/A converter 374 is dc voltage whose value is equal to $KV_o/255$ and this value is $V_{ref}$.

The sinewave generated by D/A converter 372 may be expressed as $$\frac{127\,KV_o}{128\cdot 255}\sin\frac{2\pi N}{128}$$

The output of D/A converter 372 is supplied to the positive input of an operational amplifier 376 such as a 3550 type made by Burr-Brown, operated in the unitry-gain non-inverting mode as a buffer. The output of operational amplifier 376 is identified as the oscillator output and is connected to the OSC inputs to the multiplexer of FIG. 7.

The sinewave output converter 372 is also supplied to the bridge circuit which comprises first and second operational amplifiers 378 and 380, such as 3550 types, whose positive inputs are interconnected by a resistor 382. The output from converter 372 is supplied at the junction between the positive input to operational amplifier 378 and resistor 382. The negative input to operational amplifier 378 is connected to the BRIDGE terminals of the electronic switches 330 of the multiplexer illustrated in FIG. 7 and thus via the multiplexer to the probe illustrated in FIG. 10.

The $C_x$ and $R_x$ quantities illustrated in the drawing between ground and the negative input of operational amplifier 378 indicate the unknown measurable capacitance and resistance of the body tissue being tested and which is coupled to ground as by a grounded plate arranged opposite the probe so that the breast is sandwiched between the probe and the grounded plate. Alternate grounding arrangements include a grounded plate arranged along the patient's back or electrodes clamped around the patient's wrists.

The output of amplifier 378 is coupled across a resistor 384 to the negative input of operational amplifier 380 and is also coupled across a parallel combination of a resistor 386 and a capacitor 388 to the negative input of operational amplifier 378. The negative input to amplifier 378 is also coupled to ground against a parallel combination of a resistor 390 and a variable capacitor 392. The output of operational amplifier 380 is fed back to the negative input thereof via a resistor 394. The negative input of the operational amplifier 380 is coupled via a resistor 396 to a potentiometer 398 for providing offset adjustment.

Typical component values are as follows: Resistors 382, 384 and 394–10 KOhm; Resistor 396–1.1 MOhm; Resistors 386 and 390–159 KOhm; Potentiometer 398 10KOhm; Capacitor 388–1nf; Capacitor 392–30–500 pf; Capacitor 393 -500 pf. Capacitor 392 is adjusted so that capacitors 392 and 393 together with the probe capacitance equal 1 nf.

Outputs H,I,J and K, being the four most significant bits of the output of counters 358, 360 and 362 are supplied to a 4-bit digital comparator such as a 74C85. The comparator, identified by reference numeral 400, compares the 4 bit input HIJK with compare bits supplied by the microcomputer system under program control. The compare bits are in the form of 4-bit binary words having a value between 1 and 15. When the HIJK input equals the compare bit word, the comparator detects the equality and provides an enable signal to a detector 402. Detector 402 is typically a two stage arrangement of four 8-input NAND gates such as 74C 30 and one 4-input NAND gate such as 74C20.

It is thus appreciated that 1–15 sinewave cycles can be applied to the patient before measurement commences.

Upon receipt of the enable signal EN, detector 402 performs the following logic sequence:

$$DET = EN\cdot(\overline{GFEDCBA} + \overline{GFEDCBA} + \overline{GFEDC\\BA} + \overline{GFEDCBA})$$

Thus the detector output signal DET goes to 1 four times during a measurement cycle. Each time the DET signal goes to 1 it enables a digital delay circuit 404, which also receives a clock signal f', typically at 1.28 MHz. After a predetermined number of cycles of signal f', delay 404 produces a HOLD command to a SAMPLE AND HOLD circuit 406, such as an Analog Devices AD 583 and also produces a START CONVERSION command to a 10 bit A-D converter 408 such as a Burr Brown ADC 85C-10. The SAMPLE AND HOLD circuit and the A-D converter thus are operative to sample the bridge circuit four times during each measurement cycle.

The sampling is delayed by a small amount in response to instructions from the microcomputer system under program control in order to compensate for the phase delay introduced by the sinewave generator and bridge circuitry. Compensation for this delay will be discussed hereinafter. Four digitized samples of the bridge output, identified as V 1, V 2, V 3 and V 4 are read into the microcomputer system from converter 408 for further processing.

In order that the invention will be more fully understood and appreciated, the theory of operation thereof will now be considered in detail:

During each measurement cycle, the sinewave generator produces a signal $$V_{osc} = \frac{127\,KV_o}{128\cdot 255}\sin\frac{2\pi N}{128}.$$

The bridge output will be zero if no tissue is being measured. If tissue with capacitance $C_x$ and conductance $G_x$ is being measured, the bridge is unbalanced, producing an analog voltage:

$$V_{br} = \frac{127\,KV_o}{128\cdot 255}\left(a\sin\frac{2\pi N}{128} + b\cos\frac{2\pi N}{128}\right) + V_{os}$$

where a and b are in-phase and quadrature terms related to $C_x$ and $G_x$, and $V_{os}$ is a DC offset voltage.

If one ignores the phase delay for the moment, we assume that detector 402 samples the signal $V_{br}$ at four values of N, i.e. N=0, 32, 64 and 96. The values of $V_{br}$ at these values of N are as follows:

$$N = 0\quad V_1' = \frac{127KV_o}{128\cdot 255}b + V_{os}$$
$$N = 32\quad V_2' = \frac{127KV_o}{128\cdot 255}a + V_{os}$$
$$N = 64\quad V_3' = -\frac{127KV_o}{128\cdot 255}b + V_{os}$$
$$N = 96\quad V_4' = -\frac{127KV_o}{128\cdot 255}a + V_{os}$$

The A-D converter 408 is operative to digitize the sampled bridge values, as nine bits plus the sign and provides the following four outputs multiplied by a scale factor of $511/V_o$.

The four outputs of A-D converter 408 may thus be expressed as follows:

$$N = 0 \; V_1 \approx 2Kb + 511 \frac{V_{os}}{V_o}$$

$$N = 32 \; V_2 \approx 2Ka + 511 \frac{V_{os}}{V_o}$$

$$N = 64 \; V_3 \approx -2Kb + 511 \frac{V_{os}}{V_o}$$

$$N = 96 \; V_4 \approx -2Ka + 511 \frac{V_{os}}{V_o}$$

Microcomputer system 306 under suitable program control forms the following two expressions:

$$A = V_2 - V_4$$

$$B = V_1 - V_3$$

It is a particular feature of the above expressions that the D.C. offset voltage terms are cancelled out and the respective in-phase and quadrature terms a and b are given by the following equations:

$$a = (A/4K)$$

$$b = (B/4K)$$

If one considers equation (4) hereinabove in the special case where $G = \Omega_o C$ where $\Omega_o = 2\pi$. 1 kHz and in the present case in which C = 1nf and G = 1 mmho/159, the in-phase and quadrature terms may be expressed as follows:

$$a = \frac{\frac{G_x}{G} + f^2 \frac{C_x}{C}}{1 + f^2}$$

$$b = f \frac{\left[\frac{C_x}{C} - \frac{G_x}{G}\right]}{1 + f^2}$$

where f = bridge frequency in kHz, (i.e. at 1 kHz, f = 1, at 100 Hz, f = 0.1 and so on.)

The above equations for a and b reduce to the following expressions:

$$C_x/C = a + b/f$$

$$G_x/G = a - fb$$

For the device described hereinabove, R = 1/G = 159 Kohms and f equals one of the following values: 0.1, 0.2, 0.5, 1, 2, 5 and 10.

The tissue admittance amplitude $|Y_x|$ can be expressed in terms of a and b and the bridge admittance amplitude $|Y| = (G^2 + \Omega^2 C^2)^{\frac{1}{2}}$ as follows:

$$|Y_x/Y| = (a^2 + b^2)^{\frac{1}{2}}$$

The phase angle $\phi_x$ of the admittance can be expressed as:

$$\phi_x = \tan^{-1} \Omega C_x / G_x$$

Thus it may be appreciated that by varying frequencies, one can calculate $C_x$, $G_x$, $|Y_x|$ and $\phi_x$ over a two-decade range of frequencies from 0.1 Hz to 10K Hz at each location of tissue. By frequency sweeping and scanning with the probe elements over a multiplicity of locations, one can measure both the frequency and spatial variatons of the four tissue parameters. The importance and usefulness of this technique will now be discussed.

One of the problems associated with impedance measurement at a single frequency is that the results obtained are in general dependent on external factors such as the pressure at which the probe is applied on the skin, the amount of coupling gel used, the distance between the two electrodes, i.e. the sensing electrode array and the grounded electrode at the patient's back, and their relative orientation. For example, a high measured value of capacitance at a given frequency may be due simply to the use of an excess of coupling gel.

It is clear that measurements subject to the above variables are not suitable for a screening program in which large numbers of patient's measurements are taken at different times by different operators. It is therefore necessary to provide a measurement technique and apparatus which produces reproducable and uniform results independently of the above extraneous variables.

To a large extent this problem can be overcome by examining tissue properties at several frequencies. The normalized slope of the graph relating the tissue property to frequency is independent of the frequency invariant factors mentioned above. For example, the dielectric constant in a given region of tissue can be expressed as $\epsilon_x(f)$. The capacitance measured by the apparatus of the present invention may be expressed as:

$$C_x(f) = A_x \epsilon_x(f)$$

where $A_x$ is a factor combining the frequency invariant factors such as the effective area of the probe and the effective path length travelled in the tissue. It may thus be understood that the desired tissue property is $\epsilon_x$ not $C_x$ which includes factors not related to the tissue characteristics sought to be measured. The present device measures $C_x$ at a plurality of different frequencies. If one then fits a curve through the measurements of $C_x$ as a function of frequency f or of log f one can take the derivative of $C_x$ with respect to f or to log f and devide by the value of $C_x$ at a particular frequency. The resulting quantity is independent of the above factor $A_x$.

In accordance with an embodiment of the present invention one takes measurements at the following frequencies: 0.1, 0.2, 0.5, 1, 2, 5 and 10 KHz. For the following range of 0.1–1 KHz and for the frequency range of 1–10 KHz one fits a third-order polynomial. Thus the capacitance may be expressed as:

$$C_x(u) = au^3 + bu^2 + cu + d$$

where u = log f

The solution for the coefficients a, b, c and d is obtained in terms of the measured values of capacitance. For example, over the frequency range of 1–10 KHz, the measured values of $C_x$ at 1, 2, 5 and 10 KHz may be denoted by $C_1$, $C_2$, $C_5$, and $C_{10}$. By standard techniques for solving linear equations, the coefficients are given in matrix form by:

$$\begin{bmatrix} a \\ b \\ c \end{bmatrix} = \begin{bmatrix} 11.94 & -11.94 & 4.75 \\ -20.29 & 15.54 & -4.75 \\ 8.35 & -3.60 & 1.00 \end{bmatrix} \begin{bmatrix} C_2 - C_1 \\ C_5 - C_1 \\ C_{10} - C_1 \end{bmatrix}$$

and $\quad d = C_1$

Using f=1KHz as the reference frequency, the derivative is given by $$(dC_x/du) = 3au^2 + 2bu + c$$

At 1KHz log 1=0 so that $$\left.\frac{dC_x}{du}\right|_{1kHz} = c$$

The required function is therefore $$\left.\frac{\frac{dC_x}{du}}{C_x}\right|_{f=1kHz} = \frac{c}{C_1} = \frac{8.35(C_2 - C_1) - 3.60(C_5 - C_1) + C_{10} - C_1}{C_1}$$

This is the fractional change in capacitance per decade of frequency. Also, since:

$$C_x = A_x \epsilon_x$$
$$\frac{\frac{dC_x}{du}}{C_x} = A_x \frac{\frac{d\epsilon_x}{du}}{A_x \epsilon_x} = \frac{\frac{d\epsilon_x}{du}}{\epsilon_x} = E_x$$

The expression $E_x$ is the fractional change in tissue dielectric constant per decade of frequency, which is a characteristic of the tissue.
Similarly, by substituting for tissue conductivity one obtains:

$$K_x = \frac{\frac{dG_x}{du}}{G_x} = \frac{\frac{dK_x}{du}}{K_x}$$
$$= \frac{8.35(G_2 - G_1) - 3.60(G_2 - G_1) + (G_{10} - G_1)}{G_1} \text{ at 1kHz}$$

where $\kappa_x$ is the fractional change in tissue conducting per decade of frequency; and $G_i$ is the conductance measured at frequency i.

One can carry out similar calculations for the fractional change in tissue admittance, magnitude and phase angle per decade.

The above analysis is also performed for the frequency range of 0.1 to 1 kHz. Here, the coefficients of the 3rd order polynomal fit are given in matrix form by $$\begin{bmatrix} a' \\ b' \\ c' \end{bmatrix} = \begin{bmatrix} -4.75 & 11.94 & -11.94 \\ -4.75 & 15.54 & -20.29 \\ -1.00 & 3.60 & -8.35 \end{bmatrix} \begin{bmatrix} C_{.1} - C_1 \\ C_{.2} - C_1 \\ C_{.5} - C_1 \end{bmatrix}$$
$$d' = C_1$$

The fractional change in C per decade at 100 Hz is then given by (noting that log 0.1 = −1)

$$E_x = \left.\frac{\frac{dC_x}{du}}{C_x}\right|_{0.1kHz} = \frac{+3a^1 - 2b^1 + c^1}{C_{.1}}$$
$$= \frac{-5.75(C_{.1} - C_1) + 8.35(C_{.2} - C_1) - 3.60(C_{.5} - C_1)}{C_{.1}}$$

Of course, other curve fitting techniques could be used, such as higher-order fitting for more data points or using f instead of log f or log C instead of C. However, the above illustration is an example of the type of processing which gives results relatig to the normalized change of the tissue parameters (dielectric constant and conductivity) per decade of frequency. This permits comparison and analysis of healthy and diseased tissue among different patients and allows followup for the same patient over a period of time.

As noted hereinabove, a delay is introduced by the sinewave generator and the bridge circuitry. A technique for compensating for this delay will now be described:

The ideal bridge output should be:

$$V_{br} = a \sin\Omega t + b \cos\omega t + V_{os}$$

if $127\ KV_o/128.255 = 1$

Due to the phase delay produced by the sinewave generator and bridge circuitry one obtains in reality:

$$V_{br} = a \sin(\omega t - \epsilon) + b \cos(\omega t - \epsilon) + V_{os}$$
$$= (a \cos\epsilon + b \sin\epsilon) \sin\omega t + (b\cos\epsilon - a \sin\epsilon) \cos\omega t + V_{os}$$
$$= a' \sin\omega t + b' \cos\omega t + V_{os}$$

where $\epsilon$ is a small phase error due to the phase shifts in the various linear amplifiers between the digital sinewave and the analog bridge output. Therefore if one samples $V_{br}$ at $\Omega T = 0$, $\pi/2$, $\pi$ and $3\pi/2$ one obtains:

$$V_{br\,1} = b' + V_{os}$$
$$V_{br\,2} = a' + V_{os}$$
$$V_{br\,3} = -b' + V_{os}$$
$$V_{br\,4} = -a' + V_{os}$$

Thus it may be understood that one finds a' and b' rather than a and b. To obtain a and b one can either solve the above equations numerically once $\epsilon$ is determined experimentally. For example in matrix form:

$$\begin{bmatrix} a' \\ b' \end{bmatrix} = \begin{bmatrix} \cos\epsilon & \sin\epsilon \\ -\sin\epsilon & \cos\epsilon \end{bmatrix} \begin{bmatrix} a \\ b \end{bmatrix}$$

The required a and b are found by inverting:

$$\begin{bmatrix} a \\ b \end{bmatrix} = \begin{bmatrix} \cos\epsilon & -\sin\epsilon \\ \sin\epsilon & \cos\epsilon \end{bmatrix} \begin{bmatrix} a' \\ b' \end{bmatrix}$$

Alternatively one can add a corresponding delay to the sampling signal as follows:

$$\text{Since } \omega t = \frac{2\pi f_d N_o T_d}{128} = \frac{2\pi N_o}{128}$$

wherein $N_o = 0$, 32, 64 and 96, i.e. at the sampling times, one chooses as n such that $2\pi n/128 = \epsilon$
One then samples at $N = N_o + n$ to match the phase delay due to the analog circuitry.

It will be appreciated that the invention is not limited to what has been specifically shown and described hereinabove. Rather the scope of the invention is defined only by the claims which follow:

We claim:

1. Apparatus for detecting tumors in living human breast tissue comprising:
   means for determining the dielectric constants of a plurality of localized regions of living human breast tissue including a bridge means having means for automatically nulling said brigde means while in operation; and
   means for measuring variations in said dielectric constants over a plurality of said regions and for indicating the possible presence of a tumor as a result of said measurement.

2. Apparatus for detecting tumors according to claim 1 and wherein said determining means comprises:
   probe means;
   means for applying a swept frequency signal to said probe means;
   signal processing circuitry, coupled to said bridge for providing an output indication of dielectric constant of the localized region of breast tissue associated with said probe means.

3. Apparatus for detecting tumors according to claim 2 wherein said swept frequency signal varies in frequency between 0.1 and 10 KHz.

4. Apparatus according to claim 1 and also comprising means for recording a plurality of dielectric constant patterns for subsequent reference.

5. Apparatus according to claim 1 and wherein said determining means comprises:
   probe means comprising a plurality of probe elements;
   means for providing a swept frequency signal
   switching means for selectably and sequentially connecting individual ones of said plurality of probe elements to said bridge and for connecting said probe elements not currently connected to said bridge to said means for providing a swept frequency signal; and wherein
   said indiciating means comprises a cathode ray tube display; and wherein said apparatus also comprises microcomputer controlled recording means for recording the dielectric constant information produced by said indicating means.

6. Apparatus for detecting tumors in living human breast tissue comprising:
   means for determining the dielectric constants of a plurality of localized regions of living human breast tissue; and
   means for indicating variations in said dielectric constants over a plurality of said regions, said variations indicating the possible presence of a tumor; and wherein said determining means comprises:
   probe means comprising a plurality of probe elements arranged for sensing different ones of said localized regions;
   switching means for selectably applying an electrical signal to said probe elements;
   a balancing bridge circuit coupled to said probe elements;
   and
   signal processing circuitry coupled to said balancing bridge for providing an output indication of dielectric constants of the localized regions of breast tissue associated with each of said probe elements.

7. Apparatus according to claim 6 and wherein said signal processing circuitry comprises an analog to digital converter.

8. Apparatus according to claim 6 and wherein said switching means comprises a multiplexer operated by a microcomputer.

9. Apparatus according to claim 6 and wherein said probe comprises an insulative housing and an $8 \times 8$ array of probe elements and wherein said switching means is operative to couple only one of said probe elements at a time to said bridge.

10. Apparatus for detecting tumors in living human breast tissue comprising:
    means for determining the variation of the dielectric constant of localized regions of living human breast tissue as a function of frequency of a signal applied thereto and including automatic balancing bridge means which do not require nulling for each measurement; and
    means for indicating differences in said variation over a plurality of said localized regions, said differences indicating the possible presence of a tumor.

11. Apparatus according to claim 10 and wherein said determining means comprises:
    probe means comprising a plurality of probe elements;
    means for providing a swept frequency signal;
    switching means for selectively and sequentially connecting individual ones of said plurality of probe elements to said balancing bridge and for connecting said probe elements not currently connected to said balancing bridge to said means for providing a swept frequency signal.

12. Apparatus according to claim 11 and wherein said indicating means comprises a cathode ray tube display and wherein said apparatus also comprises microcomputer controlled recording means for recording the dielectric constant variation information produced by said indicating means.

13. A method for detecting tumors in living human breast tissue comprising the steps of:
    applying probe means comprising a plurality of probe elements to human breast tissue in vivo such that individual ones of said probe elements are arranged for sensing characteristics of individual localized regions of human breast tissue;
    selectably applying an electrical signal to said probe elements for determining the dielectric constants of said localized regions of living human breast tissue; and
    detecting a possible tumor by sensing variations in said dielectric constants over a plurality of said regions.

14. A method according to claim 13 and also comprising the step of:
    determining the dielectric constants of said localized regions at a plurality of signal frequencies.

15. A method for detecting tumors in living human breast tissue comprising the steps of:
    applying probe means comprising a plurality of probe elements to human breast tissue in vivo such that individual ones of said probe elements are arranged for sensing characteristics of individual localized regions of human breast tissue;
    selectably applying an electric signal to said probe elements for determining the dielectric constants of said localized regions of living human breast tissue;

sensing variations in said dielectric constants over a plurality of said regions to indicate the possible presence of a tumor; and determining the rate of change of dielectric constant with frequency at each of said localized regions.

16. A method for detecting tumors in living human breast tissue comprising the steps of:

applying probe means comprising a plurality of probe elements to human breast tissue in vivo such that individual ones of said probe elements are arranged for sensing characteristics of individual localized regions of human breast tissue;

selectably applying an electrical signal to said probe elements for determining the dielectric constants of said localized regions of living human breast tissue;

sensing variations in said dielectric constants over a plurality of said regions to indicate the possible presence of a tumor; and determining the rate of change of dielectric constant with log of frequency at each of said localized regions.

* * * * *

UNITED STATES PATENT AND TRADEMARK OFFICE

(12)      CERTIFICATE EXTENDING PATENT TERM
UNDER 35 U.S.C. § 156

(68) PATENT NO. : 4,291,708

(45) ISSUED : September 29, 1981

(75) INVENTOR : Ephraim H. Frei

(73) PATENT OWNER : Yeda Research & Development Co.

(95) PRODUCT : T-Scan 2000 ®

This is to certify that an application under 35 U.S.C. § 156 has been filed in the United States Patent and Trademark Office, requesting extension of the term of U.S. Patent No. 4,291,708 based upon the regulatory review of the product T-Scan 2000® by the Food and Drug Administration. Since it appears that the requirements of the law have been met, this certificate extends the term of the patent for the period of

(94)      1,113 days from November 2, 1998, the original expiration date of the patent, subject to the payment of maintenance fees as provided by law, with all rights pertaining thereto as provided by 35 U.S.C. § 156(b).

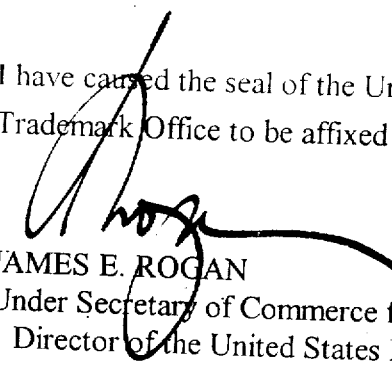

I have caused the seal of the United States Patent and Trademark Office to be affixed this 7th day of January 2004.

JAMES E. ROGAN
Under Secretary of Commerce for Intellectual Property and
Director of the United States Patent and Trademark Office